(12) United States Patent
Delos et al.

(10) Patent No.: US 8,708,920 B2
(45) Date of Patent: Apr. 29, 2014

(54) METHOD AND SYSTEM FOR DETECTING APNEA

(75) Inventors: John B. Delos, Williamsburg, VA (US); Hoshik Lee, Williamsburg, VA (US)

(73) Assignee: College of William and Mary, Williamsburg, VA (US)

( * ) Notice: Subject to any disclaimer, the term of this patent is extended or adjusted under 35 U.S.C. 154(b) by 296 days.

(21) Appl. No.: 13/214,998

(22) Filed: Aug. 22, 2011

(65) Prior Publication Data

US 2012/0172730 A1 Jul. 5, 2012

Related U.S. Application Data

(60) Provisional application No. 61/429,558, filed on Jan. 4, 2011.

(51) Int. Cl.
*A61B 5/08* (2006.01)

(52) U.S. Cl.
USPC ........................................................ 600/484

(58) Field of Classification Search
USPC ........................................................ 600/484
See application file for complete search history.

(56) References Cited

U.S. PATENT DOCUMENTS

| | | | |
|---|---|---|---|
| 4,379,460 A | 4/1983 | Judell | |
| 4,781,201 A | 11/1988 | Wright | |
| 5,503,160 A | 4/1996 | Pering | |
| 2003/0055348 A1* | 3/2003 | Chazal et al. | 600/509 |
| 2007/0118054 A1* | 5/2007 | Pinhas et al. | 600/587 |
| 2010/0331715 A1* | 12/2010 | Addison et al. | 600/529 |

OTHER PUBLICATIONS

Bloch-Salisbury, "Stabilizing immature breathing patterns of preterm infants using stochastic mechanosensory stimulation", J. Appl. Physiol. (2009), vol. 107, pp. 1017-1027.

* cited by examiner

*Primary Examiner* — Michael Kahelin
*Assistant Examiner* — Mitchell Alter
(74) *Attorney, Agent, or Firm* — Jason P. McDevitt

(57) ABSTRACT

Existing monitors for apnea miss many serious events because they do not adequately distinguish the heart signal in chest impedance from the respiratory signal. Described herein is a respiratory monitoring system and method for improved detection and response to apnea, particularly in a NICU setting but also useful in a home setting. This method filters from the chest impedance the part of the impedance that is caused by the beating of the heart in a human subject, and then identifies in real time significant silence in the filtered chest impedance signal, including determining the probability of apnea. If the probability of apnea exceeds a threshold value, the apneic subject can be stimulated using automated interactions such as a vibrating mattress or air blower.

2 Claims, 12 Drawing Sheets

METHOD AND SYSTEM FOR DETECTING APNEA

CROSS-REFERENCE TO RELATED APPLICATIONS

This application claims the benefit of and priority to U.S. Provisional Patent Application Ser. No. 61/429,558, filed Jan. 4, 2011, the entire disclosure of which is incorporated by reference herein.

STATEMENT REGARDING FEDERALLY SPONSORED RESEARCH AND DEVELOPMENT

This invention was made with government support under Grant No. NICHD 5RCZHD064489 awarded by the National Institutes of Health. The government has certain rights in the invention.

FIELD OF INVENTION

The field of the invention relates to detection of apnea, and is particularly beneficial for detection of apnea in premature infants.

BACKGROUND OF THE INVENTION

Apnea is common in premature infants, and is sometimes called apnea of prematurity. It is related to immaturity of the central nervous system, although it can also occur secondary to other causes and is a common manifestation of many neonatal diseases. It occurs in more than half of infants whose birth weight is less than 1500 g, and in almost all infants whose birth weight is less than 1000 g (see N. N. Finer et al., Pediatrics (2006) 117:S47-S51). Apnea may be a cause or an effect of many other clinical problems, such as abnormal neurological development.

Three types of apnea are common in premature infants: obstructive apnea, central apnea and mixed apnea. Obstructive apnea is a blockage of the airway, typically accompanied by struggling or thrashing movements of the infant. Central apnea is cessation of respiratory drive: the infant simply stops breathing for some period of time, and usually remains very still. Mixed apneas typically begin with an obstructive event, and then change to central apnea. In many cases, the apnea is combined with, or induces, bradycardia (a significant slowing of the heart rate). The same three types of apnea occur in adults.

All of these apneas are serious clinical events that need immediate medical attention. However, existing monitors for apnea are unsatisfactory—they miss many serious events. Typical respiratory monitors do not distinguish the heart signal in chest impedance from the respiratory signal. For this reason, they often fail to recognize apnea and therefore fail to provide a warning signal to neonatal intensive care unit ("NICU") personnel alerting them to the fact that the infant is not breathing.

Thus, there is a need in the art for improved systems and methods to provide earlier detection of apnea. The methods described herein appropriately filter out electrical fluctuations resulting from the heartbeat such that chest impedance measurements more accurately track the respiratory rate. Due to the increased detection of apnea events, in certain embodiments, automated interaction is utilized to stimulate the premature infant during an apnea event.

One way to remove the heartbeat from the chest impedance was proposed by Neil H. K. Judell in U.S. Pat. No. 4,379,460 (1983). That method assumed that the fluctuation in the chest impedance caused by the latest heartbeat is the same as that caused by the previous heartbeat. Other methods are described in U.S. Pat. Nos. 4,781,201 and 5,503,160. None of these references teaches a method of determining the probability of apnea.

BRIEF SUMMARY OF THE INVENTION

Accordingly, it is an object of the present invention to provide an improved respiratory monitoring system and method that better detects apnea, particularly in a NICU setting but also useful in a home setting.

It is also an object of the invention to provide a method that filters from the chest impedance the part of the impedance that is caused by the beating of the heart in a human subject, and then identifies in real time significant silence in the filtered chest impedance signal, including determining the probability of apnea. If the probability of apnea exceeds a threshold value, the human subject can be stimulated using automated interactions such as a vibrating mattress or air blower. Additionally, medical personnel can be alerted. Systems are also described that incorporate such an apnea detection method.

Using the EKG signal, we use the heart itself as a clock (FIG. 5). The chest impedance is re-sampled to be incremented per heartbeat. In other words, the chest impedance per second is converted to a re-sampled chest impedance signal per heartbeat. Once re-sampled, all peaks in the chest impedance signal that are caused by the heartbeat have equal spacing of one unit.

Subsequently, the Fourier transform of the re-sampled chest impedance signal has sharp narrow peaks at integer frequencies (e.g., see large peak at 1 on the x-axis in FIG. 6). The re-sampled chest impedance signal can be filtered to remove the heartbeat and low-frequency fluctuations that plainly do not represent regular breathing. Further analysis is done with this doubly filtered chest impedance signal, as described herein.

BRIEF DESCRIPTION OF THE DRAWINGS

The summary above, and the following detailed description, will be better understood in view of the drawings that depict details of preferred embodiments.

DETAILED DESCRIPTION OF THE INVENTION

The present invention is directed to a system and methods for improving detection of apnea. More specifically, the standard chest impedance signal used to monitor respiration rate is re-sampled to filter out the contribution to the chest impedance signal that arises from a beating heart, and the probability of an apneic event is calculated.

The standard method for monitoring respiration in Neonatal Intensive Care Units (NICU's) involves continuous monitoring of chest impedance. Using electrodes that are also used to monitor the electrocardiogram (EKG), a small high-frequency (e.g., 39 KHz) voltage is applied to the chest, and the resulting high-frequency current is measured. The measured impedance Z is equal to the applied voltage divided by the observed current. The measured impedance is typically in the range 50 to 300 ohms; it is related to the conductivity of muscle, skin, other tissues, and the contacts between electrodes and skin.

When the infant is breathing, the impedance fluctuates by a few ohms in each breath. Air has low electrical conductivity, and more air in the lungs gives higher impedance. The beating of the heart also gives fluctuations of impedance, of the order of half an ohm. Blood has a high conductivity, and as the heart fills, the impedance drops; each heartbeat pumps blood out of the thorax, leading to an increase in impedance.

Figure 1:
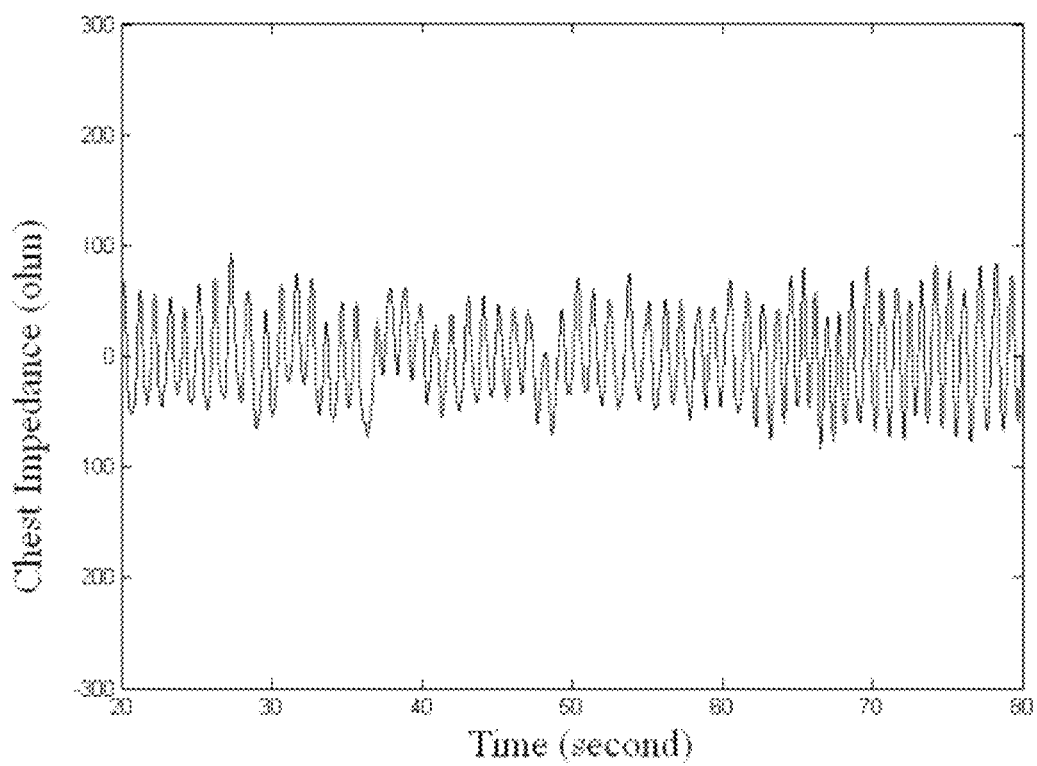
FIG. 1 is a graph showing chest impedance as a function of time during normal breathing using a prior art respiration monitor.
Figure 2:
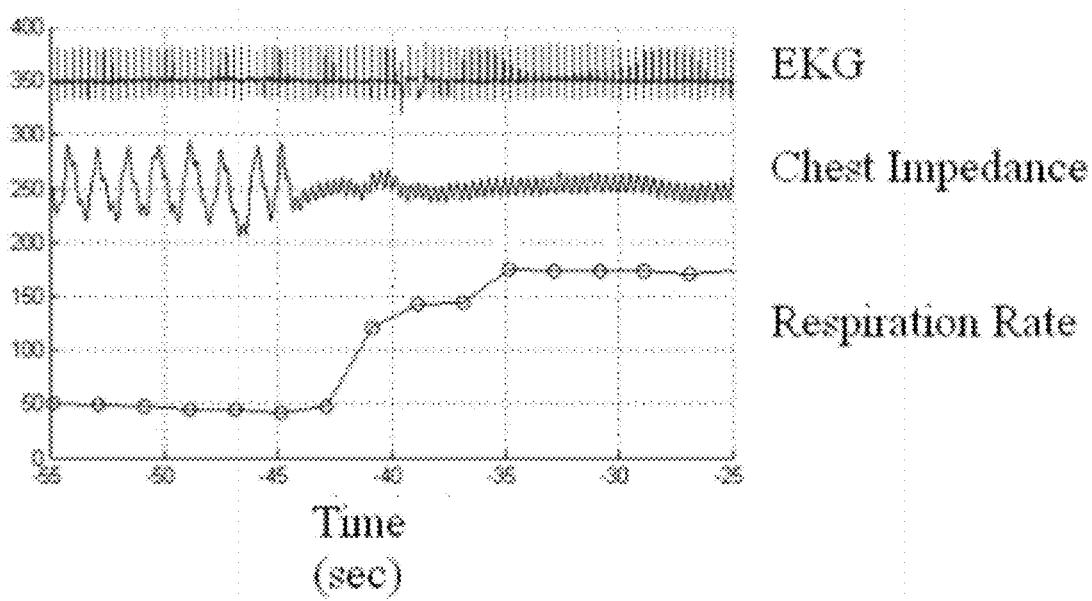
FIG. 2 is a graph showing the output of a prior art respiration monitor during onset of an apnea episode, which occurs around t=−44 seconds. The prior art monitor shows that the respiration rate of the infant increases from 50 breaths per minute to 180 breaths per minute. In fact, the infant is not breathing at all.

FIG. 1 shows one output of a prior art respiration monitor. The regular fluctuations in the chest impedance are associated with regular breathing, typically about one breath per second for NICU infants. FIG. 2 shows the beginning of an apnea event at t=−44 seconds. The chest impedance curve abruptly changes from large fluctuations at about 1 Hz to smaller fluctuations at about 3 Hz. Those 3 Hz fluctuations are caused by the beating of the heart. This infant stopped breathing for about 90 seconds, but the NICU monitor did not recognize it. Eventually the heart slowed sufficiently to set off an alarm.

Figure 3:
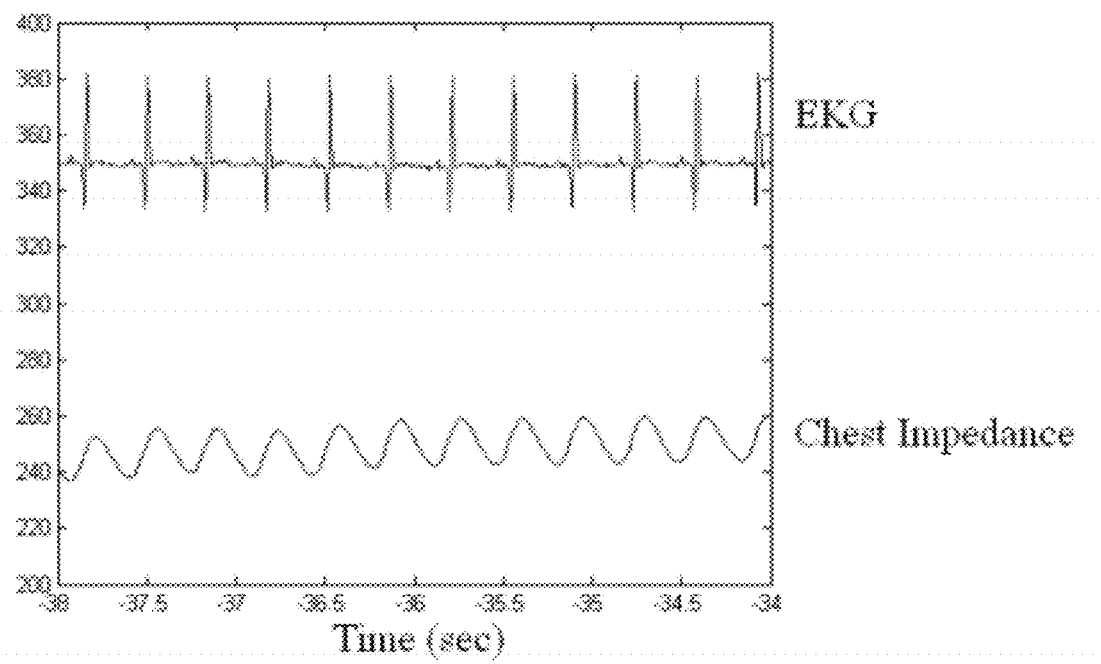
FIG. 3 shows the EKG of the same infant and event of FIG. 2. The largest peaks in the EKG are called R peaks. The lowest curve is the fluctuation in chest impedance as a function of time during the apnea episode. These plainly match the rhythm of the heart.
Figure 4:
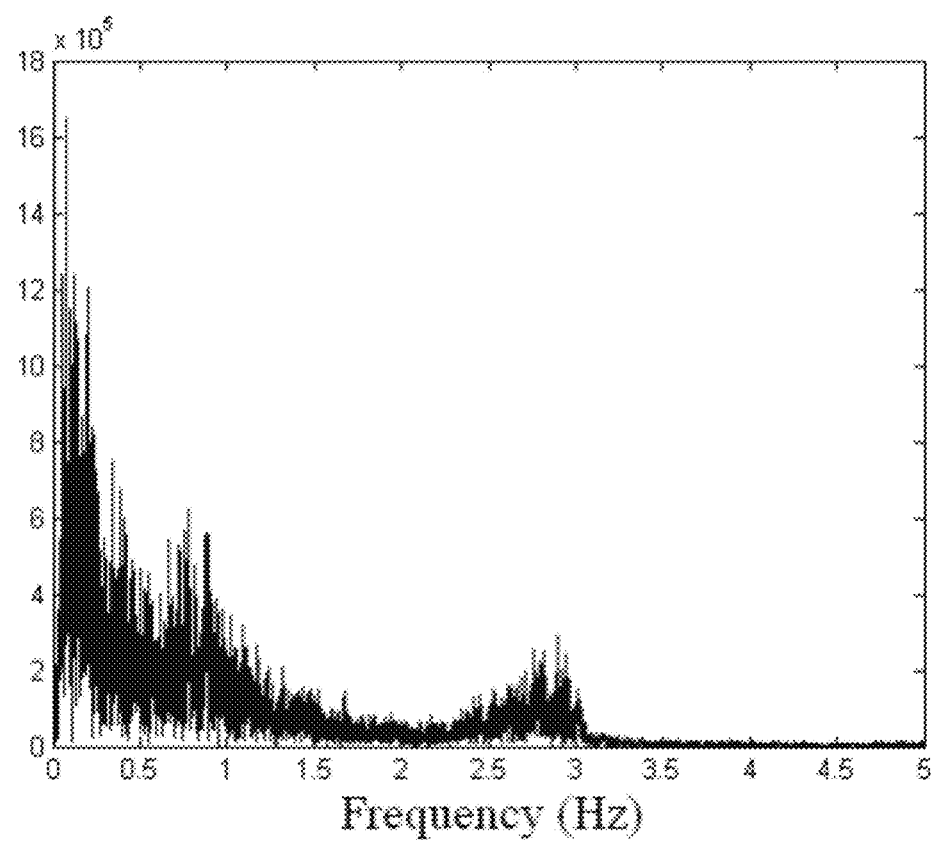
FIG. 4 is a graph showing a Fourier transform of chest impedance during an apnea event. Low and broad peaks are observed around 1 Hz and around 3 Hz, but these cannot be used effectively to filter the heartbeat from respiration.
Figure 5:
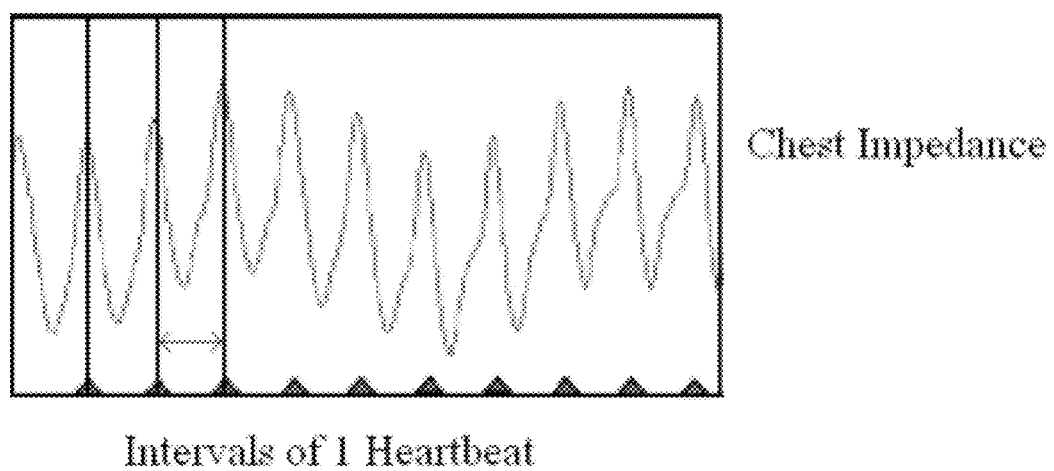
FIG. 5 shows the EKG signal of FIG. 3, whereby the intervals of measurement are stretched or contracted to be one heartbeat. By converting the chest impedance per second to a re-sampled chest impedance signal per heartbeat, the fluctuations in chest impedance cause by the heartbeat can be attenuated.

FIG. 3 shows a zoomed in portion of FIG. 2 during the apnea event. The rhythmic 3 Hz fluctuations in chest impedance match the rhythm of the EKG signal. At first glance, it might appear that a simple Fourier band-stop filter would attenuate the impedance caused by the beating heart. However, during an extended apnea event, the heart usually slows to a rate below 100 beats per minute, so the Fourier spectum of the chest impedance is broad-band, with no identifiable frequencies (see FIG. 4). Instead, using the EKG signal, we use the heart itself as a clock (see FIG. 5). The chest impedance is re-sampled to be incremented per heartbeat. The interval is stretch or contracted to fit each heartbeat. In other words, the chest impedance per second is converted to a re-sampled chest impedance signal per heartbeat. Once re-sampled, all peaks in the chest impedance signal that are caused by the heartbeat have equal spacing of one unit.

Figure 6:
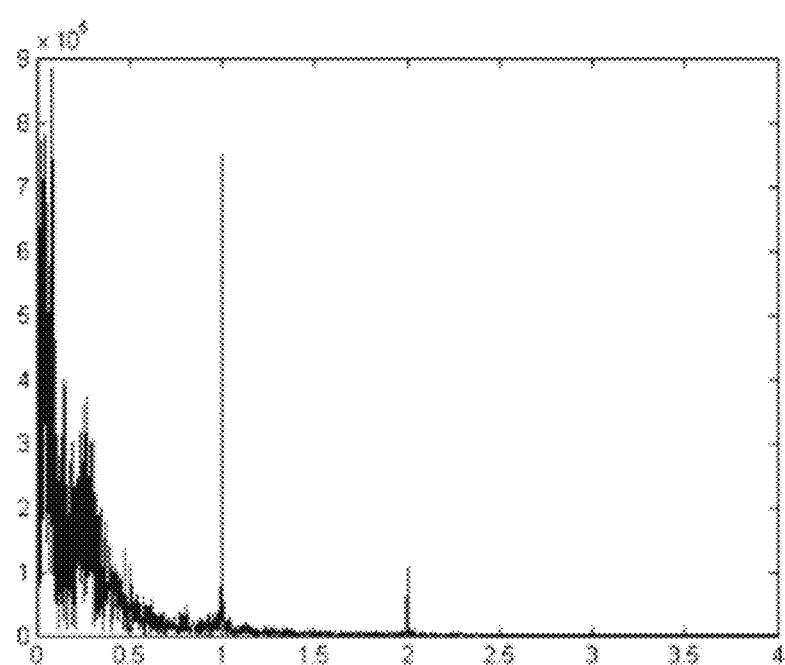
FIG. 6 is a Fourier transform of the re-sampled chest impedance signal using the heart as the clock. The impedance caused by the heart is now a set of narrow, sharp peaks at integer frequencies, such as 1.
Figure 7:
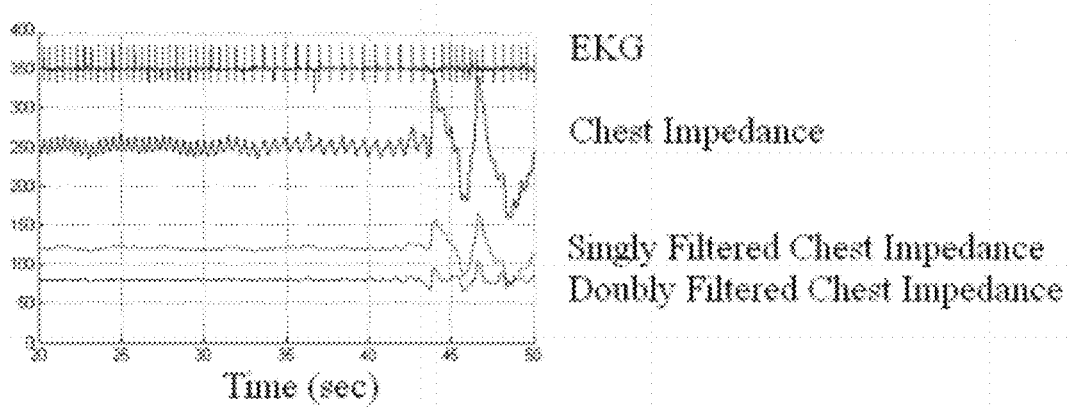
FIG. 7 is a graph showing the same infant and event as in FIG. 2, but simply at a later time. The lowest two graphs in this figure, labeled singly filtered chest impedance and doubly filtered chest impedance, represent the result of the new filtering method wherein, the signal is significantly silent during the apnea event.

Subsequently, the Fourier transform of the re-sampled chest impedance signal has sharp narrow peaks at integer frequencies (see FIG. 6). The large peak at 1 along the x-axis (i.e., one cycle per heartbeat) is due to the beating of the heart. A band-stop filter removes a segment of the Fourier transform. After filtering using the band-stop filter, the signal can be transformed back to real time to produce the "singly filtered chest impedance signal" (see the curve of FIG. 7 labeled "Singly Filtered Chest Impedance"). The singly filtered chest impedance signal is significantly silent during the apnea event. FIG. 7 is a graph showing the same infant and event as in FIG. 2, but simply at a later time. The large fluctuations in chest impedance starting near 45 seconds represent the beginning of regular breathing and the end of an apnea event.

However, after using the band-stop filter, there remains in this signal small, low-frequency fluctuations that plainly do not represent regular breathing. These small low-frequency fluctuations can be removed with a high-pass filter to produce the "doubly filtered chest impedance signal" (see the bottom curve of FIG. 7 labeled "Doubly Filtered Chest Impedance"). The doubly filtered chest impedance signal is also significantly silent during the apnea event. The signal is more silent than the singly filtered chest impedance because small low-frequency fluctuations are filtered. Converting the doubly filtered chest impedance signal back to real time can occur after the band-stop filter, between the band-stop filter and the high-pass filter, or after the high-pass filter depending on need. Further analysis is done with this doubly-filtered chest impedance signal.

A pattern recognition system for identifying and characterizing apnea is required in order to best utilize the doubly filtered chest impedance signal. While one could surmise that when this signal is silent (no fluctuations), then the infant is having apnea, the key is determining what constitutes sufficient silence to solidify a diagnosis of apnea. Chest impedance signals often have fluctuations related to movement of the infant, to random noise, and to imperfections in removal of the impedance cause by the heart beating. The strength of those artifacts can vary greatly, even over short periods of time (e.g., 10 minutes).

Figure 10:
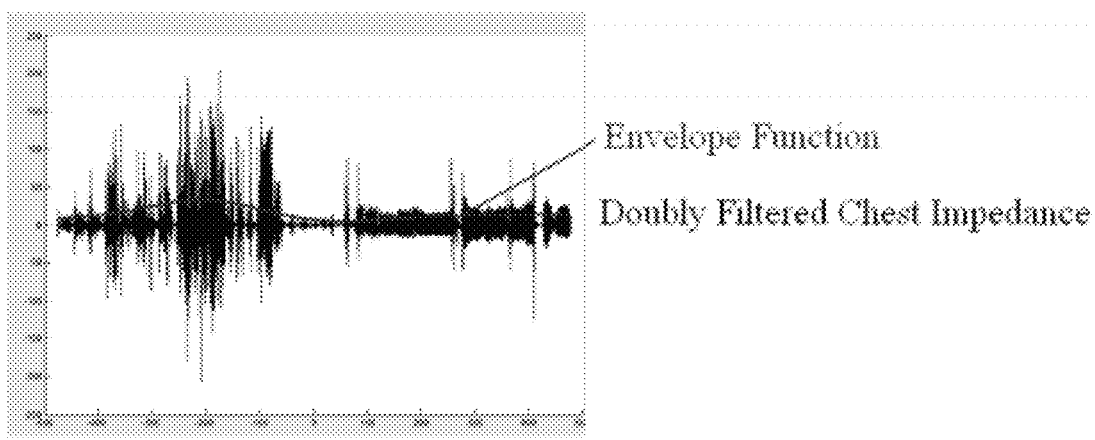
FIG. 10 is a graph depicting the doubly filtered chest impedance signal and an envelope function that is constructed using a very low-pass filter.

Consequently, we sought to develop a method for predicting the probability of apnea. Chest impedance and EKG data was collected from very apneic infants. The chest impedance data was converted to a doubly filtered chest impedance using the method as previously described. The doubly filtered chest impedance signal of the very apneic infants was re-normalized. One method for re-normalizing the signal is to divide it by an envelope function computed using a very-low-pass filter, as shown in FIG. 10. Then, a running variance $\sigma(t)$ of the re-normalized signal was computed.

Figure 8:
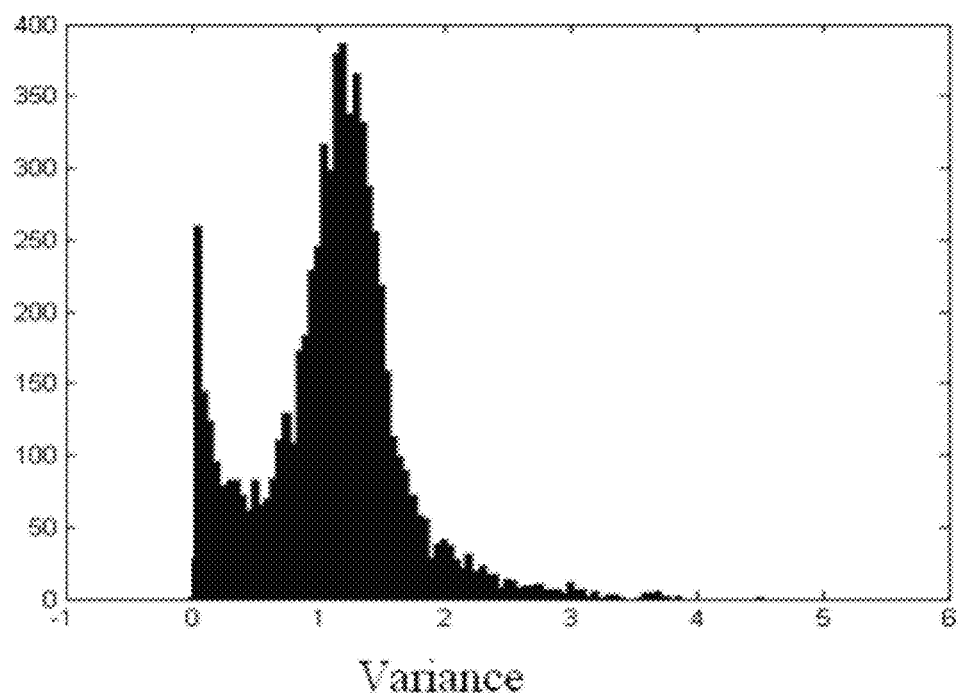
FIG. 8 is a histogram of the variance of the doubly filtered and renormalized chest impedance signal of an infant with many apneas.

A histogram of the variance of the doubly filtered and re-normalized chest impedance signal for one apneic infant is shown in FIG. 8. The variance is measured every quarter second over a two second interval for a period of four hours.

Figure 9:
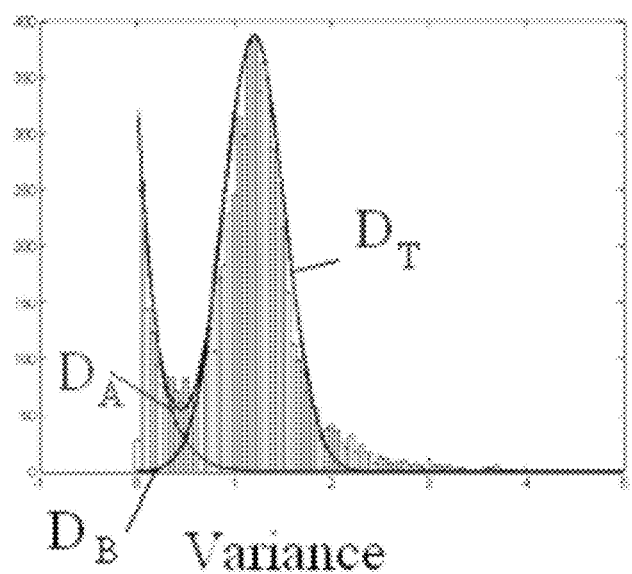
FIG. 9 shows the histogram of FIG. 8 after separating into two distributions.

We interpret this histogram as a statistical mixture of two distributions, $D_A(\sigma)$, which corresponds to the chest impedance variance during apnea, and $D_B(\sigma)$, which corresponds to the chest impedance variance during breathing. Utilizing curve fitting techniques, the two distributions can be approximated as exponential curves as shown in FIG. 9, wherein:

$$D_A(\sigma)=250\times\exp(-(\sigma-0.05)\times 5.0)$$

$$D_B(\sigma)=387\times\exp[-(\sigma-1.2)^2/(2\times 0.22)^2]$$

The curve for the total histogram is the sum of these two functions, $D_T(\sigma)$.

$$D_T(\sigma)=D_A(\sigma)+D_B(\sigma)$$

Figure 11:
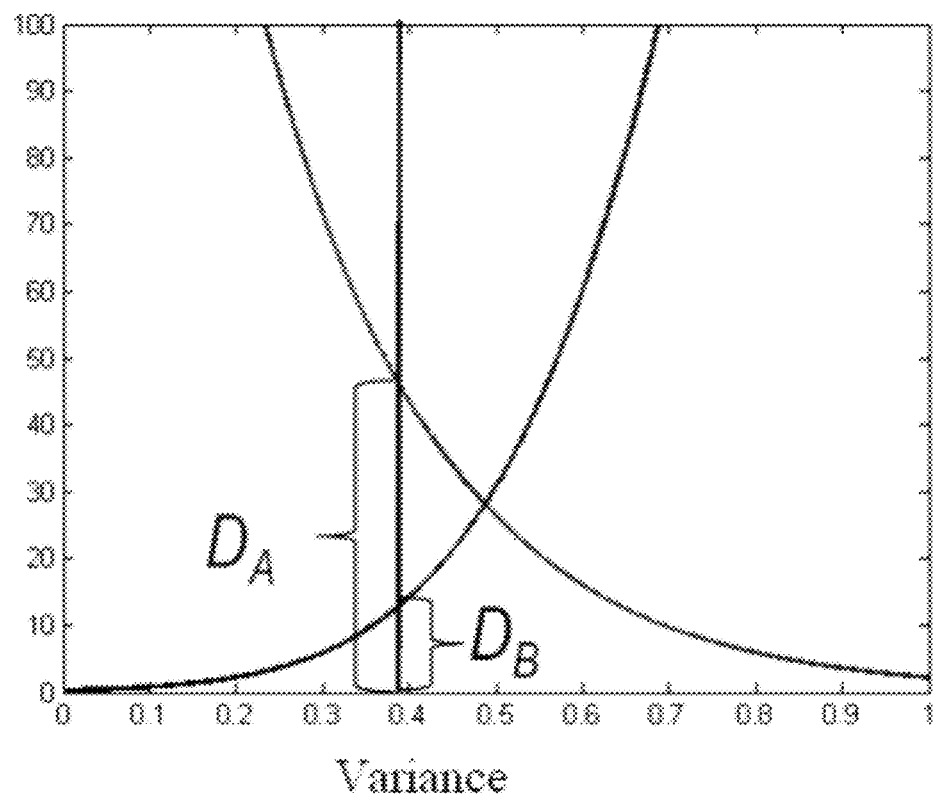
FIG. 11 is a graph depicting the probability of apnea for a specific variance in the doubly filtered chest impedance signal.

To determine the probability of apnea, the running variance of the human subject is compared to the histogram of FIG. 8. For instance, if the running variance of the human subject was 0.4 as shown in FIG. 11, then the probability of apnea would be determined by:

$$P=D_A(\sigma)/[D_A(\sigma)+D_B(\sigma)].$$

For convenience, the probability of apnea can be fit to a single function such as:

$$P_{fit}(\sigma)=1/[1+\exp(\sigma-\alpha)\beta]$$

with appropriate values for $\alpha$ and $\beta$.

Figure 12:
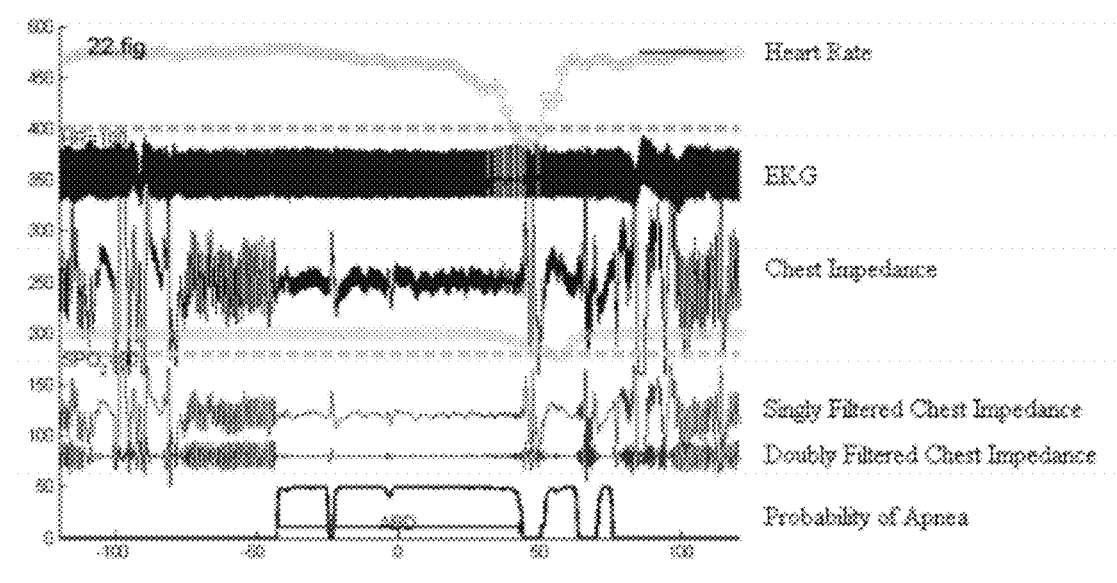
FIG. 12 is a graph showing the full data associated with the apnea event of FIG. 2, including the doubly filtered chest impedance signal and the probability of apnea.

The probability of apnea can be displayed as a signal, for example, see FIG. 12. The method of calculating the probability of apnea has been validated by comparing its results with expert analysis of hundreds of apnea events in the NICU at the University of Virginia. Parameters in the probability function $P_{fit}(\sigma)$ were refined using this validation. There is usually better than 90% agreement between our new apnea detection algorithm and the expert analysis. See also Example 2 below.

By alerting medical practitioners when the probability of apnea remains high for a selected duration, e.g., by exceeding a pre-defined threshold probability value, medical practitioners such as NICU nurses can be alerted significantly earlier during an apnea episode, potentially saving lives and reducing associated health risks.

Increasing detection of apnea events will also strain nursing staffs, and it would be advantageous to restore breathing in the apneic subject without requiring intervention from medical personnel. In one embodiment, a monitor is modified or connected to a bedside or central computer such that it is capable of re-sampling and filtering the chest impedance to the doubly filtered chest impedance signal and calculating the probability of apnea, as per the method previously described. When significant silence indicating an apnea event is detected, the monitor communicates with a means for automated interaction which stimulates the human subject. Direct communication between the monitor and the means for automated interaction may limit the interference from other devices near the human subject and be more reliable. Indirect communication (e.g., wireless) between the monitor and the means for automated interaction may allow further distance between the monitor and the human subject. Both direct and indirect communication methods are contemplated for connecting the monitor with the means for automated interaction.

The means for automated interaction could stimulate the human subject undergoing an apnea event in numerous ways. For example, the sense of touch could be stimulated, as taught by Eisenfeld in U.S. Pat. No. 5,555,891, the entire disclosure of which is incorporated by reference herein. Means for automated interaction contemplated herein include, but are not limited to, a jacket worn by the infant which squeezes, strokes, or vibrates upon activation, a mat on which the infant rests which vibrates upon activation, and a blower capable of delivering a strong puff of air which contacts the skin upon activation. Alternatively, the means for automated interaction could stimulate the sense of sound, e.g., by triggering an audible alarm.

Due to the unique nature of automated interaction, the stimulation can be gradual. The monitor modified as per the method described herein is also capable of varying the degree of stimulation. Based on continued silence of the doubly filtered chest impedance signal, the monitor can gradually increase the degree of stimulation such as gradually greater vibrations or a gradually louder sound. Alternatively, the monitor can increase the intensity of stimulation by discrete, incremental steps such as a low steady sound, followed by a medium steady sound, and then a loud steady sound. Further experimentation would be required to determine the ideal mode of stimulation.

It is contemplated that some infants will not respond to automated interactions due the severity of the apnea episode. The apnea detection system described herein can alert trained medical personnel if initial efforts of automated interaction fail. In one embodiment, this alert could occur as soon as the apnea monitoring system detects apnea. The system could commence automated interaction until personnel arrive. Additionally, the system could cancel the alert if the human subject responds to the automated interaction and begins regular breathing. In another embodiment, this alert could occur after a set period of time, for example, seven seconds, or ten seconds. The apnea monitoring system could commence automated interaction as soon as significant silence is detected. Medical personnel would be alerted after a set period of automated interaction if the subject did not respond sufficiently to the automated interaction. After the alert, the system could continue with the automated interaction until the arrival of medical practitioners. The set period of time would be determined from the typical response time of medical personnel to apnea events. The apnea detection system described herein would be calibrated such that the average response time is less than or does not exceed the average response time with currently available systems.

The method described herein for detecting apnea is being used to provide a useful history for each patient. A log of apnea events can be kept. The number of events, their duration, and the probability of apnea can be recorded as measures of the frequency and severity of apneas in each infant throughout the infant's stay in the NICU.

Likewise, the frequency, duration, and severity of oxygen desaturation and bradycardia events can be recorded. These may be correlated with each other, and with other clinical events. For example, the correlation between apnea and bradycardia can give information about the physiological control loops connecting respiration with heart rate. Additionally, such data can be used to test other medical hypotheses.

Presently, many NICU's apply an "eight-day-countdown" rule, i.e., if there are no apnea events recorded by NICU personnel for a period of eight successive days, then it may be deemed safe to release the infant to home. The method of detecting apnea described herein can be compared with the records made by NICU personnel, which may lead to better justification of this eight-day-countdown rule, or may lead to modification of the rule.

EXAMPLES

Exemplary investigations supporting the apnea detection method provided by the present invention are presented below. The examples that follow are intended in no way to limit the scope of this invention, but are provided to illustrate representative embodiments of the present invention. Many other embodiments of this invention will be apparent to one skilled in the art.

Example 1

The episode depicted in FIG. 2 and FIG. 7 is depicted in its entirety in FIG. 12. This infant stopped breathing at t~-40 s, had one gasp at t~-25 s, possibly another small gasp at t~-3 s, then stopped breathing until stimulation by NICU personnel at t~+45 s. Additional apnea events occurred until regular breathing resumed near t~+75 s. FIG. 12 shows the conversion from the doubly filtered chest impedance signal (second to bottom curve) to the probability of apnea (bottom curve). The designation "ABD" means that this was an apnea event coupled with bradycardia and oxygen desaturation. Unlike the traditional signals obtained in the NICU using prior art respiratory monitors, the singly filtered and doubly filtered chest impedance signals give rise to clear indications of an apnea episode due to the significant silence of the signal. Additionally, the probability of apnea curve at the bottom of the graph also provides a clear indication that apnea is occurring.

Example 2

In five infants with high incidences of apnea, 237 randomly selected bradycardia/oxygen desaturation events (heart rate less than 100, $SpO_2$ less than 80%) with greater than 10 seconds stopped breathing were investigated using the methods of the present invention. Three clinicians individually examined all events, and reached agreement on 234 of the 237 windows. The methods of the present invention to detect probability of apnea agreed with the clinicians on 212 of the 234 windows, a 90.6% accuracy rate. Of the 141 instances in which clinicians diagnosed that an apnea episode had occurred, the methods for detecting apnea described herein agreed with the clinicians' conclusion that an apnea episode had occurred in 132 of the instances. Of the 93 events in which clinicians agreed that an apnea episode had not occurred, the methods used herein agreed with the clinicians 86 times.

Example 3

The apnea detection system described herein was used to retroactively identify 100 random potential ABD events from a massive dataset in the University of Virginia hospital database. Of those 100 events, clinicians characterized five as false positives and 6 as real events that only had a duration of less than 30 seconds, with agreement on the other 89 events.

Example 4

The experimental approach of Example 3 above can not be used to detect false negatives. To search for false negatives, 114 apnea alarms were randomly selected from the monitoring system that is currently used at the University of Virginia hospital. Among 114 alarms produced by the monitors, the clinicians concluded that 74 of them were false alarms, a 65% false alarm rate, with 40 real events. Of the 40 real events, the apnea detection system described herein successfully detected 39 of them, a 97.5% success rate, with only a single false negative. The apnea detection system also identified 43 additional events that the clinicians concluded were not apneas. This is a substantially lower false positive rate than the monitors currently used. In all cases, these false positives occurred because the chest impedance signal was very weak.

Incorporation By Reference

All publications, patents, and patent applications cited herein are hereby expressly incorporated by reference in their entirety and for all purposes to the same extent as if each was so individually denoted.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

The articles "a" and "an" are used herein to refer to one or to more than one (i.e. to at least one) of the grammatical object of the article. By way of example, a respiratory monitor means one respiratory monitor or more than one respiratory monitor.

The term signal is used herein to refer generically to something that conveys information, notice, or warning. The signal need not be increments of time.

Any ranges cited herein are inclusive.

We claim:

1. A method for detecting and responding to apnea in a human subject comprising:
    measuring in real time the chest impedance signal and heartbeat of a human subject;
    converting said chest impedance signal per second to a re-sampled chest impedance signal per heartbeat;
    filtering said re-sampled chest impedance signal to provide a filtered chest impedance signal per heartbeat;
    renormalizing said filtered chest impedance signal;
    calculating in real time the running variance of said filtered chest impedance signal; and
    calculating a probability of apnea from a histogram compiled from the running variance of the filtered chest impedance signal for a set of apneic infants;
    wherein said histogram is interpreted as a statistical mixture of a first distribution corresponding to apnea events and a second distribution corresponding to regular breathing, and said first distribution divided by the sum of said first distribution and second distribution produces a probability of apnea for each variance; and
    wherein said filtered chest impedance signal attenuates the impedance caused by the heartbeat.

2. The method of claim 1, wherein the method correctly identifies at least 90% of apnea occurrences compared with expert analysis.

* * * * *